| United States Patent [19] | [11] Patent Number: 4,915,939 |
| Iwahashi | [45] Date of Patent: Apr. 10, 1990 |

[54] REACTION TYPED DEODORANT COMPOSITION HAVING A CORROSION-INHIBITING ACTIVITY

[75] Inventor: Takashi Iwahashi, Sagamihara, Japan

[73] Assignee: Aikoh Co., Ltd., Tokyo, Japan

[21] Appl. No.: 219,386

[22] Filed: Jul. 15, 1988

[51] Int. Cl.$^4$ .................................................. A61L 9/01
[52] U.S. Cl. .............................. 424/76.21; 424/76.1; 424/76.5; 424/76.6
[58] Field of Search ................... 424/76, 76.21, 76.1, 424/76.5, 76.6

[56] References Cited

U.S. PATENT DOCUMENTS

| 4,067,262 | 2/1971 | Bowers | 424/76.7 |
| 4,172,123 | 10/1979 | Lowicki | 424/76.4 |
| 4,294,821 | 10/1981 | Neumiller | 424/76.2 |

FOREIGN PATENT DOCUMENTS 0142559 8/1987 Japan .................................. 424/76.9

Primary Examiner—Thurman K. Page
Assistant Examiner—Archene A. Turner
Attorney, Agent, or Firm—Larson and Taylor

[57] ABSTRACT

A deodorant composition is now provided, which comprises at least one of alcoholic amine compounds, at least one of organic zinc compounds and water, the proportion of each component being 1% to 60% by weight of alcoholic amine compound per 100% by weight of the composition, 0.1% to 40% by weight of organic zinc compound and the remainder of water. The deodorant composition according to this invention may efficiently be used not only to deodorize acidic bad odors but also to inhibit corrosion of steel material.

2 Claims, No Drawings

REACTION TYPED DEODORANT COMPOSITION HAVING A CORROSION-INHIBITING ACTIVITY

SUMMARY OF THE INVENTION:

This invention relates to a new, reaction typed, corrosion-inhibiting deodorant composition which may primarily be used by spraying or dusting it directly on the sources of bad odors at the treatment of sewage, dust and industrial wastes or by the addition thereof to foul-smelling chemicals or insecticides, and which is very effective for deodorizing acidic odor-generating substances such as hydrogen sulfide, methyl mercaptan, dimethyl sulfide or sulfur dioxide as well as to inhibit the corrosion of steel material which is attributed to acidic substances contained in the sources of bad odors.

BACKGROUND OF THE INVENTION:

There are already known a lot of patent literatures relating to deodorant compositions which may mainly be classified into the four species mentioned below.
(i) deodorizer which appeals to human's sense, i.e. odor feeling.
(ii) deodorizer which exhibits deodorization activity due to physical adsorption action.
(iii) deodorizer which exerts deodorization activity by the use of microorganism.
(iv) deodorizer which shows deodorization activity due to the mechanism of chemical reaction.

More specifically, the deodorizer of the first type is the one which utilized a masking method by fragrant materials. According to the nature of bad odors, however, this method has a drawback that unpleasant bad odors may sometimes be promoted by the fragrant materials employed. Moreover, the deodorizer of the second type contains an active carbon as main ingredient and so has a disadvantage that it is poor to moisture content. Furthermore, the deodorizer of the third type suffers from drawbacks that it does not produce immediate deodorization effect and is often difficult to control under appropriate conditions.

Whereas, the deodorizer of the fourth type has remarkable advantages that it takes fast-acting deodorization effect, is very easy to handle and safe by the appropriate choice of active reagent to be used and may cause the desired deodorization efficiency to be ensured. As typical examples of the active reagents previously used in the reaction typed deodorizer, now, there may be mentioned inorganic salt substances such as sodium hydroxide, potassium hydroxide, sodium carbonate, potassium carbonate, iron chloride, iron sulphate, zinc chloride, zinc sulphate, copper sulphate and lead sulphate. Amongst those reagents as listed above, however, the iron compounds are poor in deodorization efficiency against acidic odor-generating substances such as hydrogen sulphide and methylmercaptan admitting that they have no problem on use. Besides, the other inorganic active compounds suffer from an inconvenience that attention must be paid on the handling and reservation thereof admitting that they are good on the deodorization effect against hydrogen sulphide. Further, there was not found in the prior art any deodorant composition which exhibits not only high deodorization activity against acidic bad odors but also excellent inhibition activity against corrosion of steel material.

We, the present inventors, have made extensive researches in an attempt to seek for such deodorant composition as dissolving above problems, and we have now found that there may be obtained a novel, reaction typed, corrosion-inhibiting deodorant composition which comprises at least one of alcoholic amine compounds, at least one of organic zinc compounds and water in specific proportions.

DETAILED DESCRIPTION OF THE INVENTION:

According to an aspect of this invention, therefore, there is provided a corrosion-inhibiting, reaction typed deodorant composition which comprises at least one of alcoholic amine compounds, at least one of organic zinc compounds and water, the proportion of each ingredient being 1% to 60% by weight of alcoholic amine compound per 100% by weight of the composition, 0.1% to 40% by weight of organic zinc compound and the remainder of water.

As typical examples of the alcoholic amine compounds employed in the deodorant composition according to this invention, there may be mentioned the following:

Monoethanolamine, diethanolamine, triethanolamine, 1-amino-2-propanol, 1,1'-aminobis,-2-propanol, 1,1,'1"-nitrilotri-2-propanol, 2-methylaminoethanol, 2-dimethylaminoethanol, 2-(2-aminoethoxy)ethanol, 2-{(2aminoethyl)amino}ethanol, 2-diethylaminoethanol, 2butylaminoethanol, 2-dibutylaminoethanol, 2-cyclohexylamincethanol, 2,2'-(methylamino)bis-ethanol, 2,2'-(butylamino)bis-ethanol, 1-methylamino-2-propanol, 1-dimethylamino-2-propanol, 1-(2-aminoethylamino)-2-propanol, 1,1'-(methylimino)bis-2-propanol, 3-amino-1-propanol, 3-dimethylamino-1-propanol, 2-amino-1-butanol, 1-ethylamino-2-butanol, 4-diethylamino-1-butanol, 1-diethylamino-2-butanol, 3-amino-2,2-dimethyl-1-propanol, 2,2-dimethyl-3-dimethylamino-1-propanol, 4-diethylamino-2-butyn-1-ol and 5-diethylamino-3-pentyne-2-ol.

As illustrative examples of the organic zinc compounds used in the deodorant composition according to this invention, there may also be enumerated the following:

Zinc formate, zinc acetate, zinc propionate, diethylzinc, zinc oxalate, zinc citrate, zinc tartrate, zinc salicylate, zinc benzoate, zinc lactate, zinc oleate, zinc stearate, zinc phenolsulphonate, zinc 2-ethylhexanoate and zinc (II) acetylacetonate.

In preparing the deodorant composition according to this invention, at least one alcoholic amine compound and at least one organic zinc compound are respectively selected from those two groups listed above, and then mixed and diluted with water. In the deodorant composition of this invention, the lower limit of the concentration of the alcoholic amine compound and of organic zinc compound should be set to 1% by weight and 0.1% by weight based on the total weight of the composition, respectively. Below the lower limit values given to the alcoholic amine compound and the organic zinc compound, therefore, the resultant deodorant composition is poor in practical effect when used as the reaction typed, corrosion-inhibiting deodorant composition for which this invention is to be intended. Above the upper limit values of 60% by weight and 40% by weight given to each component, further, the resultant deodorant composition does not result in any further improvement in deodorization activity and corrosion-inhibiting activity and so the upper limit of the concentration of each component should be set to the specific one as mentioned above.

The proportion by weight of water in the deodorant composition will selectively be determined according to the solubility of each component chosen from the said two groups and the conditions for the composition to be used.

The alcoholic amine compound used in the deodorant composition according to this invention occurs, because of its basicity, a neutralization reaction with an acidic odor-generating substance such as hydrogen sulfide, but exhibits a slow deodorization effect on the lower concentration of hydrogen sulfide below 10 ppm. On the contrary, the organic zinc compound employed in the deodorant composition of this invention reveals a very efficient and immediate deodorization effect against from higher to lower concentration of hydrogen sulfide.

In case when the deodorant composition is to be used as spray into atmospheric air for the removal of hydrogen sulfide gas therefrom, for example, the alcoholic amine compound cannot exert an ample deodorization capacity. Unless reaction takes place with the acidic substance in an aqueous solution, the deodorization reaction between the alcoholic amine compound and the acidic substance is not good. An exception to this case, is where the reaction product of the alcoholic amine compound with the acidic substance to be deodorized, is dissolving in the aqueous solution. In fact, the higher the concentration of the unreacted hydrogen sulfide or of the said reaction product in the aqueous solution, namely the lower the water content in the aqueous solution, the lower the reaction efficiency is between the alcoholic amine compound and hydrogen sulfide.

Whereas, zinc sulfide, one of the reaction products of organic zinc compound with hydrogen sulfide is hardly soluble in water and exhausted as precipitate out of the aqueous system. So the reaction efficiency between organic zinc compound and hydrogen sulfide is almost never lowered and the organic zinc compound may react sufficiently with hydrogen sulfide even in the presence of atmospheric moisture.

Furthermore, the alcoholic amine compound is also employed to neutralize an organic acid, i.e. the other one of the reaction products of organic zinc compound with hydrogen sulfide. As a typical example of such deodorization and neutralization reactions, there may be mentioned the following equation (A) which corresponds to deodorization reaction where zinc acetate is reacted with hydrogen sulfide to afford zinc sulfide and acetic acid, and equation (B) which corresponds to neutralization reaction wherein acetic acid is reacted with alcoholic amine compound to afford the neutralized reaction product.

(A)

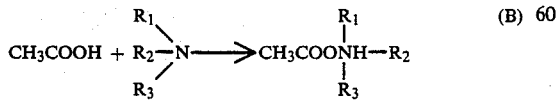

(B)

wherein at least one of $R_1$, $R_2$ and $R_3$ represents a saturated or unsaturated aliphatic hydrocarbon group containing a hydroxyl group, and the remainder is hydrogen or a lower alkyl group.

The acetic acid resulted from the equation (A) is also an acidic substance similar to hydrogen sulfide and often the object of aversion because of its particular smell. Therefore, the neutralization reaction according to the equation (B) gives this problem a solution.

Besides, the alcoholic amine compound employed in the deodorant composition of this invention has in its molecule the following skeleton structure:

wherein $R_1$, $R_2$ and $R_3$ are as defined above. An electron pair which the nitrogen atom in the said structure possesses is prone to be adsorbed on a surface of a metal such as steel stock. By virtue of occurrence in this adsorption, the surface of the steel stock is totally coated with a molecule of alcoholic amine compound thereby to prevent the surface from corroding due to the acidic substance.

This invention is further illustrated with reference to the following Example to which this invention is in no way limited and which demonstrates an excellent deodorization efficiency as well as corrosion-inhibiting activity of the deodorant composition of this invention.

EXAMPLE

The deodorant compositions according to this invention were formulated and shown in the following Table 1.

TABLE 1

| | (based on % by weight) | | | | |
|---|---|---|---|---|---|
| | Component | | | | |
| | Alcoholic amine compound | | Organic zinc compound | | |
| Sample No. | Diethanol-amine | 2-Diethyl-amino-ethanol | Zinc acetate | Zinc citrate | Water |
| 1 | 55.0 | — | — | 2.5 | 42.5 |
| 2 | — | 20.0 | 5.0 | — | 75.0 |
| 3 | 10.0 | — | — | 30.0 | 60.0 |
| 4 | — | 2.0 | 0.5 | — | 97.5 |

When the deodorant composition in Table 1 comprised as active ingredient zinc acetate alone, for example, such a deodorant composition was unfit for actual use because zinc acetate was often the object of aversion due to its acetic acid smell. When the deodorant composition contained as active ingredient, zinc acetate in combination with the alcoholic amine compound, however, unpleasant acetic acid smell was completely suppressed and the pH value of the deodorant solution could be maintained alkaline. Therefore, good results were given to the deodorization efficiency against acidic odor-generating substances such as hydrogen sulfide and methylmercaptan by the use of the deodorant composition containing both the alcoholic amine compound and organic zinc compound according to this invention.

Sample Nos. 1 to 4 as given in Table 1 were tested on their deodorizing activities. The test results concerning deodorization rate (%) is summarized in Table 2 below. The test procedure employed was as follows: Hydrogen sulfide, methylmercaptan, diemthylsulfide and sulfur dioxide, respectively, was used as offensive smelling gases to be tested for deodorization, and those bad odor gases were adjusted to each concentration of 100 ppm (parts per million) by dilution with nitrogen gas and charged into separate 2000 ml-tightly sealable containers into which were also introduced 10 ml portions of the deodorant compositions according to this invention as shown in the above Table 1. The content-filled containers were tightly closed and then shaken for a period of 5 minutes. Finally, the concentration of the bad odor gas remaining in the containers was determined by using the Kitagawa typed detecting tube, and deodorization rate (%) was calculated from the difference between the initial concentration before the addition of the deodorant and the finally determined concentration after the addition of the deodorant.

TABLE 2

| Sample No. | Components of bad odors & Deodorization rate (%) | | | |
|---|---|---|---|---|
| | Hydrogen sulfide | Methyl-mercaptan | Dimethyl-sulfide | Sulfur dioxide |
| 1 | 100 | 70 | 65 | 100 |
| 2 | 100 | 60 | 60 | 100 |
| 3 | 100 | 70 | 65 | 100 |
| 4 | 60 | 30 | 25 | 60 |

The following experiment was further carried out in order to ensure that the deodorant composition according to this invention was also effective for inhibiting corrosion of steel material.

Pieces of carbon steel sheet, the size of 50 mm ×50 mm ×1.0 mm (JIS G3101 SS41) were used as specimens for the corrosion-inhibiting test. The surfaces of these carbon steel sheets were abraded with an abrasive-coated paper No. 320, immersed in 2% by weight solution of neutral detergent, and washed moderately therein with a sponge, washed with water and then immersed in alcoholic solution for 10 minutes and in acetone for 10 minutes. Subsequently, these pieses of sheets were maintained in a dryer at 40° C. for one hour, allowed to cool within a desiccator for one hour, and weighed previously up to a unit of 0.1 mg.

Next, three types of immersion solutions for corroding the said test specimens were prepared, as shown in Table 3 below.

TABLE 3

| Species | Composition | | | |
|---|---|---|---|---|
| | Ion-exchanged water | Aqueous solution of hydrogen sulfide | Sample No. 3 | Total amount (ml) |
| Solution (A) | 150 | — | — | 150 |
| Solution (B) | 20 | 130 | — | 150 |
| Solution (C) | — | 130 | 20 | 150 |

In Table 3, the aqueous solution of hydrogen sulfide in water was used at a concentration of 500 ppm. Then, the said two pre-treated test specimens were charged into every three 200 ml-beakers to which the respective immersion solutions given in Table 3, had been added, and which were tightly closed immediately and allowed to stand for a period of three days in a thermostatic chamber at 25° C. Three days later, the test specimens were removed from the thermostatic chamber, washed with water moderately, using a sponge, immersed in alcohol for 10 minutes and in acetone for 10 minutes, and then allowed to stand in a dryer at 40° C. for one hour and in a desiccator for one hour, and finally weighed precisely. By using the determined values thus obtained, the proportion of the corroded steel sheet (mg/cm$^2$) was calculated from the following formula:

The proportion of the corroded steel sheet (mg/cm$^2$) = {Weight of the test specimen before immersion (mg) — weight of the test specimen after immersion (mg)}/Surface area of the test specimen (cm$^2$).

The corrosion test as mentioned above was effected by the use of the said immersion solution, and the proportion of the corroded steel sheet was summarized in Table 4 below. Each numerical value in Table 4 was an average value obtained from the two test specimens.

TABLE 4

| Species | Weight of test specimen before immersion (g) | Weight of test specimen after immersion (g) | Proportion of corrosion (mg/cm$^2$) |
|---|---|---|---|
| Solution (A) | 27.3470 | 27.3330 | 0.27 |
| Solution (B) | 26.7170 | 26.6631 | 1.04 |
| Solution (C) | 26.6265 | 26.6240 | 0.05 |

As abvious from Table 4 above, the proportion of the corroded test specimen when immersed in Solution (C) is fairly lower than that obtained by immersion in Solution (A) or (B), and so this result proved that a significantly remarkable effect on inhibition against corrosion of the test specimen was achieved with the Sample No. 3 into which the deodorant composition of this invention was incorporated.

As mentioned above, the reaction typed deodorant composition according to this invention will obviously be effective not only for deodorization against acidic odor-generating substances such as hydrogen sulfide, methylmercaptan, dimethysulfide and sulfur dioxide but also for inhibition against corrosion to steel stocks such as steel sheet and steel tubing, which is attributed to acidic substances present in the sources of bad odor, the latter activity being resulted from the nitrogen-containing compound, alcoholic amine compound which is one of the active ingredients in the deodorant composition of this invention.

What I claim is:

1. A corrosion-inhibiting deodorant composition for use in the spraying or dusting on sources of acidic bad odors during treatment of sewage, dust and industrial wastes which consists essentially of at least one alcoholic amine compound selected from the group consisting of diethanol amine, triethanolamine and 2-diethylaminoethanol, at least one organic zinc compound selected from the group consisting of zinc lower alkyl monocarboxylate and zinc lower alkyl tricarboxylate said lower alkyl group having 1-7 carbon atoms and water, the proportion of each ingredient being 1% to 60% by weight of alcoholic amine compound per 100% by weight of the composition, 0.1% to 40% by weight of organic zinc compound and the remainder water.

2. A deodorant composition according to claim 1 wherein the zinc compound is zinc acetate or zinc citrate.

* * * * *